US00PP14019P39

(12) United States Plant Patent
Flagler

(10) Patent No.: US PP14,019 P3
(45) Date of Patent: Jul. 29, 2003

(54) PLUM TREE NAMED 'EARLY DANAE'

(76) Inventor: George Flagler, P.O. Box 68, Parlier, CA (US) 93648

( * ) Notice: Subject to any disclaimer, the term of this patent is extended or adjusted under 35 U.S.C. 154(b) by 64 days.

(21) Appl. No.: 09/908,876

(22) Filed: Jul. 18, 2001

(65) Prior Publication Data

US 2003/0018999 P1 Jan. 23, 2003

(51) Int. Cl.[7] ..... A01H 5/00
(52) U.S. Cl. ..... Plt./184

(58) Field of Search ..... Plt./184

*Primary Examiner*—Bruce R. Campell
*Assistant Examiner*—Susan B. McCormick
(74) *Attorney, Agent, or Firm*—Mark D. Miller

(57) ABSTRACT

A new variety of plum tree which is remotely similar to the unpatented 'Early Beaut' plum tree but is distinguished from it by producing uniformly purple skin coloration fruit which are mature for harvesting and shipment one week earlier than the 'Early Beaut' plum tree and exhibits superior holding capacity than the 'Early Beaut' plum tree and having more yellow flesh throughout.

1 Drawing Sheet

BACKGROUND OF THE NEW VARIETY

This present invention relates to a new and distinct variety of plum tree which will hereinafter be denominated varietally as the 'Early Danae' plum tree and more particular to a plum tree which produces fruit which are mature for commercial harvesting and shipment about May 20–25 in the San Joaquin Valley of Central California and which is further distinguished from one of its parent 'Showtime' plum tree (U.S. Plant Pat. No. 8,037) in that it produces fruits that have a dark purple skin coloration which can be retained on the tree and remains firm to a high level of maturity. In addition, the flesh of the fruit of this invention is a yellow gold color throughout with the shape of the fruit being somewhat flatter at the stem end.

ORIGIN AND ASEXUAL REPRODUCTION OF THE NEW VARIETY

The present variety was discovered as an open, pollinated hybrid of the 'Showtime' plum tree (U.S. Plant Pat. No. 8,037) in a sixteen acre plum orchard located approximately ½ mile south of Manning Avenue in Parlier, Calif. The grafting of the scion wood of the new invention took place at that location. The grower has observed this invention since 1999 and confirmed that distinctive characteristics of the parent tree are precisely reproduced in the progeny.

SUMMARY OF THE NEW VARIETY

The 'Early Danae' plum tree is characterized as to novelty by producing a medium size fruit generally of dark purple skin coloration, ripe for commercial harvest and shipment approximately May 20–25 in the San Joaquin valley of Central California. The new and novel variety is an open pollinated hybrid of the 'Showtime' plum tree (U.S. Plant Pat. No. 8,037) from which it is distinguished principally by producing a uniformly dark purple skin fruit of medium size and having generally a yellow gold flesh coloration throughout as compared to the red flesh color of 'Showtime' with fruit shape more globular with a somewhat more flattened stem end than 'Showtime,' ripe for commercial harvest and shipment approximately three to four weeks before the 'Showtime' plum tree fruit, and the 'Early Danae' remains on the tree up to a high level of maturity.

BRIEF DESCRIPTION OF THE DRAWING

The accompanying drawing is a color photograph showing mature fruit of the new variety of plum tree of the present invention, including fruit showing just the ventral side of the fruit. The second plan shows the stem end (bottom view of the fruit). The third plan shows the apex end. The fourth plan shows the fruit sectioned along the suture plant with the stone removed exposing the flesh and the pit in the cavity. The final plan shows the foliage and twig of the new variety displaying the upper and lower surface of the leaves.

DETAILED DESCRIPTION

Referring to more specific pomological details of this new and distinct variety of plum tree, the following has been observed under the ecological conditions prevailing at the orchard of origin which is located near Parlier in the San Joaquin Valley of Central California. All major color code designations are by reference to the Dictionary of Color by Maerz & Paul, First Edition 1930. Common color names are also occasionally used.

TREE

Rootstock: The observed plant was propagated and grown on Nemaguard rootstock.

Size: Medium, similar in size and growth habit to 'Showtime' (U.S. Plant Pat. No. 8,037) — typical size for plum trees (approximately 10–12 feet in height, and from approximately 8–10 feet in width, depending upon cultural practices, fertilization, pruning, soil conditions, climate, watering, temperature, girdling and available space).

Vigor: Good at 3$^{rd}$ year of growth.

Figure (form): Upright and spreading with open vase system of training. Productivity is good to very good for tree in 3rd year of growth. Regularity of bearing appears to be regular (i.e. every year, not alternate years).

Trunk size:
*Stocky*.—Diameter 20 inches, 18 inches above soil level, somewhat shaggy.
*Color code*.—Sandy beige (14-A-3).
*Lenticels*.—Oval form, small and short. Color Code — Brown (56-L-2). Number — Numerous.
Branches:
*Size*.—Medium — 9 inches in diameter, 40 inches above ground; angle 35–38°.
*Surface texture*.—Mature — Somewhat shaggy. Immature — Smooth.
*Color code* (*one year of older*).—Cattail café noir (8-H-12).
*Color code* (*immature*).—Parrot green (21-L-6).

LEAVES

Size: Medium.
Length: 95–105 mm (3.74–4.13 inches).
Width: 35–40 mm (1.38–1.57 inches).
Shape: Lanceolate having a tapering apex as a tapering base.
Texture: Smooth.
Color code: Upwardly disposed surface (upper side) — Hunter green (24-C-11). Downwardly disposed surface (underside) — Near civette green (22-L-8).
Marginal form: Double serrated.
Leaf vein: Color Code — Kildare green (19-I-5).
Venation patten: Pinnate.
Thickness: 1 mm (0.039 inches).
Glandular characteristics: Globular.
*Color code*.—Green (23-L-1).
*Size*.—Small (1 mm in length — 0.039 inches).
*Number*.—Two.
Petiole:
*Size*.—Medium.
*Length*.—12–15mm (0.472–0.590 inches).
*Diameter*.—2 mm (0.078 inches).
*Color code*.—Kildare green (19-I-5).

FLOWERS

Flower buds: Hardy under ecological conditions in the San Joaquin Valley.
Size: 5 mm (0.193 inches) long, 3 mm (0.118 inches) wide.
Form: Conic.
Bud scales: Color Code — Forest Green / Cypress Green (23-L-6).
Generally: Showy.
Date of bloom: 10% as of February 25–26, 40% bloom as of February 28–30. It is not comparable to parent.
Size: Small.
Diameter: Fully expanded — 20–22 mm (0.787–0.866 inches).
Bloom quality: Abundant.
Fragrance: None.
Petals:
*Size*.—Small, 5 in number. Length — 7–9 mm (0.276–0.350 inches). Width — 8 mm (0.315 inches).
*Form*.—Broadly ovate.
*Color code*.—Annapolis White (40-C-6).
*Apex*.—Semi round.
*Base*.—Slightly rounded.
*Petal claws*.—Broadly truncate. Length — less than 1 mm (0.039 inches). Width — 1 mm (0.039 inches).
*Petal margins*.—Round with undulated margins.
*Flower pedicel*.—Very short, 1 mm (0.039 inches). Color Code — Kildare green (19-I-5). Surface — Slightly pubescent. Diameter — 2 mm (0.079 inches).
Sepals:
*Surface*.—Pubescent.
*Size*.—Medium to large, 2–3 mm (0.079–0.120 inches).
*Form*.—Broadly ovate.
*Color code*.—Forest Green / Cypress Green (23-L-6).
*Number*.—Five.
Calyx: Color Code — vetiver green (22-G-1) at base.
Anthers:
*Size*.—Small.
*Color code*.—Sea green (11-G-7).
Stamen: Very small, less than 1 mm (0.039 inches). Number — 22–25.
Pistil:
*Length*.—Small on average.
*Number*.—1.
*Color code*.—Yellow gold (18-I-5).
*Surface*.—Pubescent.

FRUIT

Date of maturity: May 20–25 in a normal year.
Size: Medium to Large.
*Diameter axial plane*.—54–65 mm (2.126–2.558 inches).
*Transverse in suture plane*.—48–57 mm (1.89–2.244 inches).
*Transverse at right angle to suture plane*.—41–45 mm (1.64–1.773 inches).
*Average fruit weight*.—4 ounces (4 fruit per pound).
Form: Uniform, symmetrical.
Suture: Shallow and inconspicuous, but occurs from apex to stem end of fruit.
Ventral surface: Smooth.
Stem cavity:
*Shape*.—Generally acute.
*Width*.—10–12 mm (0.394–0.472 inches).
*Depth*.—12 mm (0.472 inches).
*Length*.—16–18 mm (0.63–0.709 inches).
Stem length: 10 mm (0.394 inches).
Apex: Shaped slightly indented.
Pistil point: Not prominent, variable in position.
Skin: Thin for plums.
Texture: Smooth but somewhat tough, not easily ruptured.
Tendency to crack: None observed.
Pollination: With graft limb of Fortune or Dell; generation is pinnate.
Color codes:
*Blush color*.—None observed, since this fruit is a dark color.
*Ground color*.—Burgundy (56-E-8).
*Flesh color*.—Empire (9-K-3).
*Color at surface of pit cavity*.—Sunflower dandelion (9-L-4).
*Color of pit well*.—Sunflower dandelion (9-L-4).
Juice production: Juicy.
Flavor: Very good.
Aroma: Moderate.
Texture: Medium firm, meaty.
Fibers:
*Number*.—Few.
*Texture*.—Firm.
Ripening: Even.

Eating quality: Very good.
Stone:
*Attachment*.—Semi-cling.
*Fibers*.—None to few.
*Size*.—Short. Length — 18 mm (0.709 inches). Width — 19 mm (0.748 inches). Diameter — 9 mm (0.354 inches).
Form: Generally oval.
Apex: Round with small point.
Color code: When Dry — Near capucine buff (9-G-5).
Bases: Slightly rounded.
Sides: Generally equal.
Texture: Grooves on both sides of the pit.
*Ridges*.—Dorsal edge smooth with ventral edge winged from base to apical.
*Tendency to split*.—None known.
*Use*.—Fresh market.
Quality:
*Ripening quality*.—Good.
*Resistance to disease*.—Unknown as of this times.
*Shipping and handling qualities*.—Good, with winter hardiness of the plum tree; not susceptible to damage during dormant season and no evidence of heat damage during the growing season.

The above description of this new variety of plum tree is based on the growing conditions prevalent near Parlier, Calif., in the Central San Joaquin Valley of California; variations of the usual magnitude, such as differences in maturity date and production, may be due to cultural practices including irrigation, fertilization, pruning, fruit thinning and primary climate changes. Typical production for a single tree during year 2000 was seven 28-pound cartons.

I claim:

1. A new and distinct variety of plum tree as described and illustrated which is remotely similar to the unpatented 'Early Beaut' plum tree but is distinguished from it by producing uniformly purple skin coloration fruit which are mature for harvesting and shipment one week earlier than the 'Early Beaut' plum tree and exhibits superior holding capacity than the 'Early Beaut' plum tree and having more yellow flesh throughout.

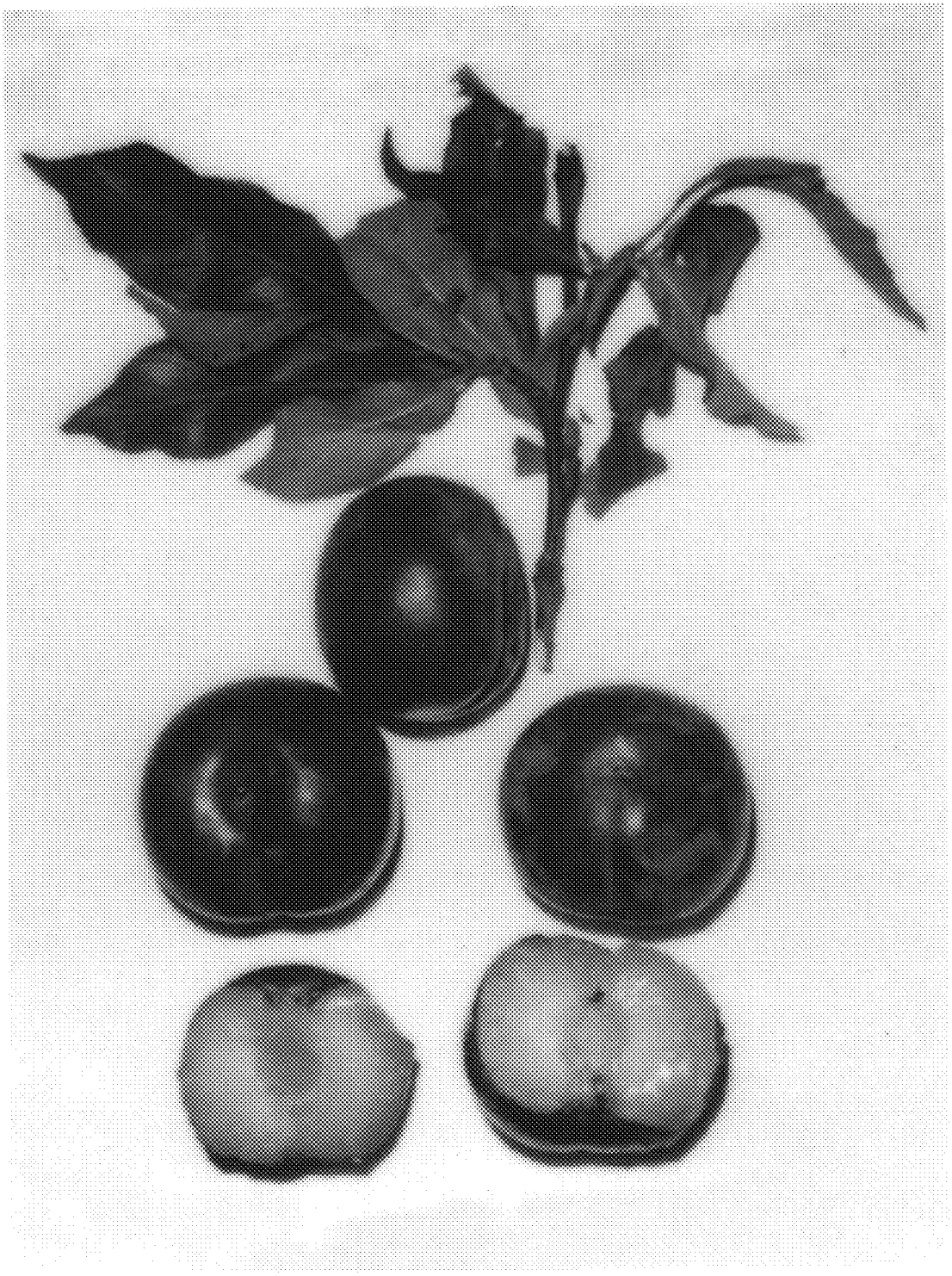

* * * * *